(12) United States Patent
Diemer

(10) Patent No.: US 7,703,671 B2
(45) Date of Patent: Apr. 27, 2010

(54) MONITORING DEVICE AND SECURITY SYSTEM

(75) Inventor: Joel A. Diemer, Las Cruces, NM (US)

(73) Assignee: Arrowhead Center, Inc., Las Cruces, NM (US)

( * ) Notice: Subject to any disclaimer, the term of this patent is extended or adjusted under 35 U.S.C. 154(b) by 0 days.

(21) Appl. No.: 11/221,599

(22) Filed: Sep. 7, 2005

(65) Prior Publication Data

US 2007/0228145 A1 Oct. 4, 2007

Related U.S. Application Data

(60) Provisional application No. 60/648,107, filed on Jan. 28, 2005.

(51) Int. Cl.
G06Q 40/00 (2006.01)
G07D 11/00 (2006.01)
G07F 19/00 (2006.01)
G06K 7/00 (2006.01)

(52) U.S. Cl. .................................... 235/379; 235/438

(58) Field of Classification Search ................ 235/379, 235/492, 380, 384, 376, 449, 487; 194/202, 194/207, 213; 705/1, 855; 340/539.1, 539.11, 340/540; 378/69; 707/1; 435/287.1; 436/1; 702/22; 73/863.81; 232/45
See application file for complete search history.

(56) References Cited

U.S. PATENT DOCUMENTS

| | | | |
|---|---|---|---|
| 4,883,264 A * | 11/1989 | Yoshikawa et al. ........... 271/110 |
| 5,237,778 A * | 8/1993 | Baer ........................... 451/326 |
| 5,269,947 A | 12/1993 | Baskis | |
| 5,461,654 A | 10/1995 | Grodzins et al. | |
| 5,807,113 A | 9/1998 | Groeber | |
| 5,963,650 A * | 10/1999 | Simionescu et al. ........... 705/63 |
| 6,087,114 A * | 7/2000 | Rider ........................... 435/7.2 |
| 6,309,827 B1 | 10/2001 | Goldstein et al. | |
| 6,312,914 B1 | 11/2001 | Kardos et al. | |
| 6,319,724 B1 | 11/2001 | Lewis et al. | |
| 6,447,991 B1 | 9/2002 | Daitch | |
| 6,481,263 B1 | 11/2002 | Haley et al. | |

(Continued)

OTHER PUBLICATIONS

Anderson, Norman G., "Global Screening for Human Viral Pathogens", *Emerging Infectious Diseases*, vol. 9, No. 7, (Jul. 2003),768-771.

(Continued)

Primary Examiner—Thien M. Le
Assistant Examiner—Thien T Mai
(74) Attorney, Agent, or Firm—Vidal A. Oaxaca; Diane E. Albert; Deborah A. Peacock

(57) ABSTRACT

The present invention provides for an integrated global biological activity detection, traffic tracking and scheduling, and boundary/border security system. Detection apparatuses of the system are preferably placed in a stream of currency such as in financial institutions and other sites of currency exchange, and are also placed in or about transportation vehicles and linked into a data collection, analysis, and graphical information system to provide early warning for security activities. Detection apparatuses located in and about transportation vehicles are combined with a system for routing vehicles into security corridors and with a system of notification, scheduling, and monitoring to enhance the capacity of authorities to insure security and efficient trade movement particularly as it approaches boundaries and borders.

24 Claims, 5 Drawing Sheets

U.S. PATENT DOCUMENTS

| | | | |
|---|---|---|---|
| 6,481,624 B1* | 11/2002 | Hayduchok | 235/449 |
| 6,672,133 B1 | 1/2004 | Maswadeh et al. | |
| 6,729,196 B2 | 5/2004 | Moler et al. | |
| 6,730,212 B1 | 5/2004 | Yamagishi et al. | |
| 6,796,896 B2* | 9/2004 | Laiti | 454/229 |
| 6,801,595 B2 | 10/2004 | Grodzins et al. | |
| 6,815,668 B2 | 11/2004 | Miller et al. | |
| 6,867,044 B2* | 3/2005 | Cordery et al. | 436/1 |
| 6,870,234 B2 | 3/2005 | Brewer et al. | |
| 6,905,885 B2 | 6/2005 | Colston | |
| 6,928,143 B2* | 8/2005 | Menear et al. | 378/69 |
| 6,997,374 B2* | 2/2006 | Stradley et al. | 232/45 |
| 7,032,467 B2* | 4/2006 | Yoon | 73/863.81 |
| 7,034,678 B2* | 4/2006 | Burkley et al. | 340/539.13 |
| 7,102,514 B2* | 9/2006 | Berry | 340/540 |
| 7,109,859 B2* | 9/2006 | Peeters | 340/539.11 |
| 2001/0029793 A1 | 10/2001 | Moler | |
| 2002/0169386 A1 | 11/2002 | Johnson, Jr. | |
| 2003/0108460 A1* | 6/2003 | Andreev et al. | 422/186.07 |
| 2003/0138344 A1* | 7/2003 | Mielnik et al. | 422/2 |
| 2003/0153021 A1 | 8/2003 | Lu et al. | |
| 2003/0157538 A1 | 8/2003 | Krull et al. | |
| 2003/0174810 A1* | 9/2003 | Korenev et al. | 378/69 |
| 2003/0234366 A1 | 12/2003 | Basch et al. | |
| 2004/0005715 A1 | 1/2004 | Schabron et al. | |
| 2004/0025963 A1 | 2/2004 | Squirrell et al. | |
| 2004/0026491 A1 | 2/2004 | Beckert et al. | |
| 2004/0204915 A1 | 10/2004 | Steinthal et al. | |
| 2004/0220753 A1 | 11/2004 | Tabe | |
| 2004/0232054 A1 | 11/2004 | Brown et al. | |
| 2005/0019757 A1 | 1/2005 | Stolarchuk | |
| 2005/0055330 A1* | 3/2005 | Britton et al. | 707/1 |
| 2005/0118704 A1* | 6/2005 | Malobabic | 435/287.1 |
| 2005/0128074 A1* | 6/2005 | Culpepper et al. | 340/539.1 |
| 2005/0177317 A1* | 8/2005 | Hsiung et al. | 702/22 |
| 2005/0276458 A1* | 12/2005 | Jones et al. | 382/135 |
| 2006/0139178 A1* | 6/2006 | Lopez et al. | 340/632 |

OTHER PUBLICATIONS

Ashley, Steven, "Silicon Sniffer", *Scientific American*, (Sep. 19, 2005),28-29.

Staedter, Tracy, "Garbage into Oil", *Technology Reveiw*, (Jun. 2003),73.

* cited by examiner

MONITORING DEVICE AND SECURITY SYSTEM

CROSS-REFERENCE TO RELATED APPLICATIONS

This application claims the benefit of the filing of U.S. Provisional Patent Application Ser. No. 60/648,107, entitled "Biological Monitoring and Security System", filed on Jan. 28, 2005, and the specification of that application is incorporated herein by reference.

BACKGROUND OF THE INVENTION

1. Field of the Invention (Technical Field)

The present invention relates to security systems for monitoring and detecting threats from toxic or dangerous substances, including biological and chemical activity and threats, in a timely manner to allow for taking effective responsive measures to forestall or mitigate the implied threat to humans, animals, economies, etc., and in combination with such detection to the management and monitoring of the transportation of goods in response to such threats.

2. Background Art

Monitoring biological activity has historically been a rather ad hoc process. Virtually all extant monitoring systems rely on networks of health professionals to identify and report animal and human disease outbreaks. At the global and regional scale, organizations (e.g., the World Health Organization (WHO), the Food and Agriculture Organization (FAO), the World Organization for Animal Health (OIE), the International Red Cross, the United State's Centers for Disease Control (CDC), and USDA APHIS National Center for Animal Health Surveillance) attempt to monitor the status of animal and human diseases and health but their efforts are slow, reactive, and heavily reliant on spotty infrastructure and unreliable human commitment.

The outbreak of Sudden Acute Respiratory Syndrome (SARS) in China's Guangdong province in 2003 demonstrates the inadequacy of relying on networks of health professionals in a fast paced, highly mobile, global community. The corona virus responsible for SARS was apparently endemic to the Guangdong region's animal population, but it was not possible to detect any anomaly that would have provided an alert as to when it had entered the human population. Even in the absence of human morbidity and fatalities, it would not likely have been part of the historic background "noise" accompanying the stew of human pathogens routinely present in the region.

Typically, the places most vulnerable to problems from diseases and to threats from hazardous substances are those that have the fewest resources to apply to such problems. But even the relatively more affluent, resource rich places with the financial and personnel resources to deal with threats often cannot intervene with those resources quickly enough to be truly effective. For example, the typical approach is to look for sick animals and sick people, but by the time those are detected, it is generally too late for truly proactive measures, particularly when, for example, pathogens are novel.

To monitor diseases, hazardous substances, and their threats more effectively, there is a need for a monitoring system that is virtually everywhere, provides information that is location specific, delivers essentially real-time data, does not rely on overt human intervention at detection points, and is relatively inexpensive to implement and maintain.

Such threats are of particular concern with respect to the transportation of goods. The essentially random arrival of freight at Mexico/US border crossings (as well as other border crossings) creates problems similar to those that would occur if international airline flights arrived randomly at international airports with no warning and inadequate documentation of their origins. When traffic arrives at border crossings, it is visually inspected (or temporarily held and visually inspected). Assuming no problems are detected during the inspection and/or holding period, traffic is passed for travel into Mexico or the United States. Consequently, every hour of every day animals (and people) that have diseases, but are asymptomatic, move through the border without incident.

Traffic scheduling by border authorities to eliminate or minimize congestion does not exist. Attempts to document the origin and destination of livestock shipments are relatively recent, far from comprehensive, and essentially of little value. Improvements in the bill-of-lading procedures have been proposed by agricultural officials but have not been adopted to date. Given the paucity of origin-destination information, lack of real-time bio-mapping, and in the final analysis, any real infrastructural capacity to respond, the isolation by point of origin to minimize cross contamination is not viable.

To ensure that the border is both secure and open in at least one location virtually all of the time, an alternative and substantially different physical layout from the current "line in the sand" is needed. Such an alternative system must incorporate a capacity for ready implementation of the newest of a wide array of rapidly developing security technologies, and it must simultaneously overcome the issues of congestion and delays while providing a high level of security.

BRIEF SUMMARY OF THE INVENTION

The present invention comprises an integrated global biological activity detection, tracking, and boundary/border security system. The global biological activity detection element of the integrated system preferably comprises a multifunctional detection apparatus (or multifunctional detector) (including, but not limited to, global positioning functionality, internet and/or proprietary bi-directional data transmission functionality) for identifying/extracting signatures for biological agents or other targeted substances (e.g., chemical, radiological) from currency as it is passed through counters at financial and other institutions throughout the world.

The system preferably comprises a secure process and infrastructure for transmitting data identified/extracted from the currency to a central data processing facility at which appropriate software and hardware for processing the data in real time to screen out background noise and isolate and identify targeted agents or substances or anomalous activity. Preferably, there are provided processes and appropriate infrastructure for mapping information extracted from the collected data to a multilayered geographical information system (GIS) for informing security operations on the ground. Preferably a command facility where data mapped to the GIS is displayed to graphically inform security operations in real time regarding biological (or other targeted substance) threats and to integrate that information with multiple other layers of geography specific data on weather, topography, institutional capacity to respond, demographics, geo-politics, etc.

The traffic tracking and scheduling component of the integrated system preferably comprises a border traffic scheduling and monitoring process and infrastructure that function in a manner analogous to international civilian air traffic control, i.e., all ground transport traffic intending to transit international or other controlled borders is required to file a transit plan at point of origin, such plan to include information on content of shipment, preferred border transit point and transit time. The information in combination with data from central data processing facility is used to inform border security authorities who are responsible for designation of a transit route including en-route check points, and time window for arrival and subsequent border transit.

The boundary/border security component of the integrated system generally and preferably includes an ultra high security border crossing infrastructure and inspection process for screening traffic in anticipation of crossing the border to enter the adjacent country or jurisdiction. Such infrastructure and processes preferably comprise a physically secure ground transit corridor of varying geographical dimensions, preferably sufficiently large enough as to require a vehicle approximately one hour to transit through the corridor while moving at a speed of at least approximately 20-30 miles an hour. The system preferably comprises a number of redundant, multi-functional sensor devices for identifying/extracting signatures for biological agents or other targeted substances, e.g., chemical, radiological, that may exist in the cargo holds, or other cavities, of vehicles proposing to transit the border, and contained in modular, plug-in units that insert into standardized receptacles incorporated as appropriate for their detection purposes into the structure of the vehicles and their cargo holding areas. The system preferably comprises a system and appropriate infrastructure for transmitting data extracted by the multifunctional sensors on board transiting vehicles, receiving, processing and responding to the results of the data analyses in real time.

The system preferably comprises protocols and appropriate physical infrastructure for diversion of vehicles with problematic cargos from the main transit corridor(s) into secure isolated locations for additional security inspection without disrupting other traffic in transit through the corridor. Preferably, there are provided protocols and appropriate facilities for the containment and where appropriate destruction and disposal of cargos (including live animals) found to be contaminated with pathogens or other dangerous or toxic materials and appropriate facilities for the detoxification and clean-up of the vehicles involved.

Thus, an embodiment of the present invention provides a system for monitoring the activity of a targeted substance on comprising an apparatus for processing a stream of currency, and at least one multifunctional detection apparatus comprising at least one sensor for detecting and identifying a targeted substance on the currency. The system may further comprise a targeted substance attraction component disposed in the currency to enhance detection by the at least one multifunctional detection apparatus. The system may further comprise a currency counter through which the stream of currency passes and in which the at least one multifunctional detection apparatus is disposed.

The system detection apparatus preferably comprises at least one component for communicating with a global positioning system, the Internet, or bi-directional data transmission systems. The at least one detection apparatus is preferably disposed at financial institutions and sites of currency exchange through which the stream of currency passes.

The system preferably further comprises a central data processing facility in communication with the at least one detection apparatus and a secure communications transmission infrastructure linking the at least one detection apparatus with the central data processing facility. The central data processing facility preferably comprises computing components for processing data received from the at least one detection apparatus in real time to screen out background noise and to isolate and identify the targeted substance.

The system preferably further comprises a mapping infrastructure for receiving information from the central data processing facility and for mapping the information to a multi-layered geographical information system in communication with security personnel.

The system preferably further comprises a central facility linking the multilayered geographical information system to security personnel to, in real time, graphically communicate the mapping information to the security personnel and to integrate the information with geographic specific data. The geographic specific data may include, but is not limited to, weather data, topography data, security response capability data, demographic data, geo-political data, agricultural data, or a combination thereof.

The system of preferably further comprises a purging apparatus for removing the targeted substance from the currency.

Another embodiment of the present invention provides a traffic tracking and scheduling system comprising a physically secure ground transit corridor through which a vehicle is directed for transit, at least one multifunctional detector disposed on the vehicle, the detector comprising at least one sensor to detect a targeted substance, an infrastructure in communication with the detector, the infrastructure for transmitting data extracted by the at least one detector and, in real time, receiving, processing, and responding to results of data analyses, and a GPS in communication with the detector. The corridor preferably comprises dimensions to accommodate a vehicle for approximately one hour when the vehicle is moving at from between approximately 20 and 30 miles per hour.

The further preferably comprises a physical infrastructure for diverting the vehicle with a targeted substance from the secure ground transit corridor to a secure isolation location for additional security inspection without disrupting other traffic in transit through the secure ground transit corridor. The at least one detector is preferably disposed in a modular unit placed in a receptacle incorporated into a structure of the vehicle.

The system preferably further comprises a facility for containment and inactivation of a target substance.

The system further preferably comprises an infrastructure for a filing of a transit plan by a transporter and a receipt of the transit plan by personnel authorized for monitoring and regulating transportation.

Another embodiment provides a targeted substance activity detection system comprising a multifunctional detection apparatus for detecting and identifying a targeted substance disposed in a stream of currency, a GPS in communication with the detection apparatus, and a multi-layered GIS system in communication with the GPS to map data received from the detection apparatus and the GPS and in communication with security personnel. The system further preferably comprises a purging apparatus to remove the targeted substance from the currency stream.

Another embodiment of the present invention provides a method for monitoring the activity of a targeted substance comprising, providing at least one multifunctional detection apparatus comprising at least one sensor for detecting and identifying a targeted substance, disposing a stream of currency in the detection apparatus, and detecting the targeted substance on the currency. The method preferably further comprises disposing a targeted substance attraction component in the currency to enhance detection by the multifunctional detection apparatus. The method preferably further comprises providing a currency counter, disposing the at least one multifunctional detection apparatus in the currency counter, passing the stream of currency through the currency counter, and detecting the targeted substance on the currency.

The method preferably further comprises communicating between the at least one detection apparatus and a global positioning system, the Internet, or proprietary bi-directional data transmission systems. The targeted substance preferably comprises a biological, a chemical, or a radiological substance. The method preferably further comprises detecting the targeted substance at financial institutions and sites of currency exchange through which the stream of currency passes.

The method preferably further comprises communicating between a central data processing facility in communication with the at least one detection apparatus and linking the detection apparatus with the central data processing facility via a secure communications transmission infrastructure. The method preferably further comprises disposing computing components in the central data processing facility and processing data received from the at least one detection apparatus in real time to screen out background noise and to isolate and identify the targeted substance. The method preferably further comprises linking a mapping infrastructure with the central data processing facility, sending information from the central data processing facility to the mapping infrastructure, and mapping the information to a multilayered geographical information system in communication with security personnel.

The method preferably further comprises providing a central facility linking the multilayered geographical information system to security personnel, graphically communicating the mapping information to the security personnel in real time, and integrating the information with geographic specific data in real time. The geographic specific data preferably comprises, but is not limited to, weather data, topography data, security response capability data, demographic data, geopolitical data, agricultural data, or a combination thereof.

The method preferably further comprises purging the currency stream to remove the targeted substance from the currency stream.

Another embodiment of the present invention provides a method for regulating and monitoring border traffic and traffic scheduling comprising requiring a vehicle required to file a transit plan at point of origin, the plan comprising information regarding cargo, preferred border transit point, and transit time, communicating the information to a border security authority, transporting the vehicle through a physically secure ground transit corridor, disposing at least one multifunctional detector comprising at least one sensor on the vehicle, placing an infrastructure in communication with the at least one detector, transmitting data extracted by the at least one detector from the infrastructure and, in real time, receiving, processing, and responding to the results of data analyses, and linking a GPS with the at least one detector.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations pointed out in the appended claims.

BRIEF DESCRIPTION OF THE SEVERAL VIEWS OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings.

DETAILED DESCRIPTION OF THE INVENTION

Figure 1:
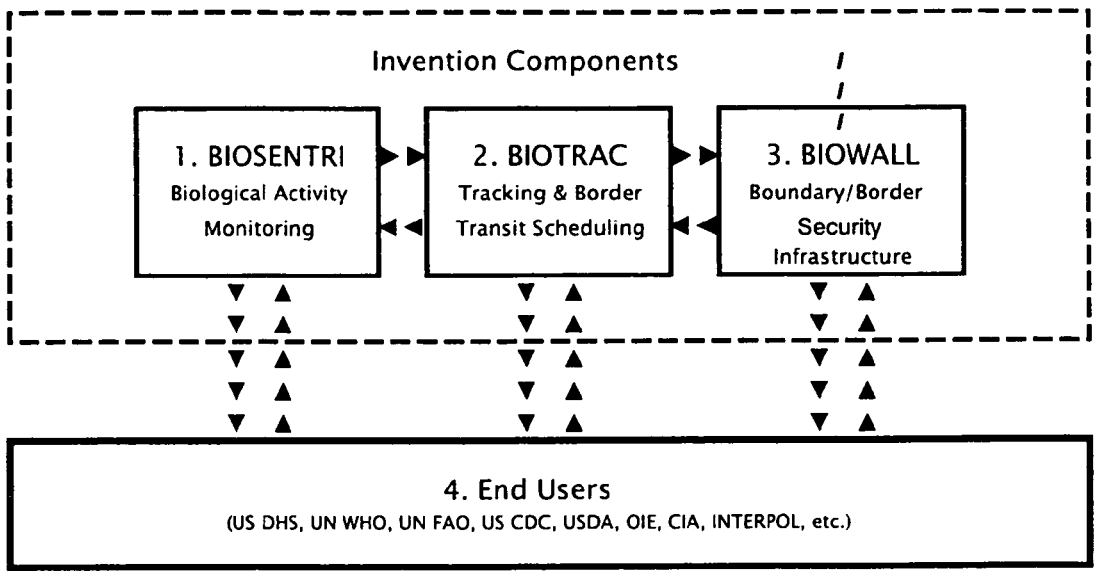
FIG. 1 is a schematic of an embodiment of the present invention showing the relationship of the primary components.

The present invention provides for a system comprising integrated, global, hazardous substance and activity detection, traffic tracking and scheduling, and boundary/border security. As used herein, "hazardous substance" is defined as any substance that is hazardous or toxic, or is a hazardous threat, to animal or human health, whether of biological, chemical, radioactive, or other nature, or is a targeted substance (e.g., drugs, chemicals, etc.). For illustrative purposes, biological substances and threats are discussed herein as representative of such hazards, although the terms "hazardous" and "biological" are used interchangeably throughout. Being the targets of detection, such hazardous and biological substances are also referred to herein as "targeted substances".

Thus, an embodiment of the present invention provides for a biological substance and activity detection system comprising lab-on-chip apparatuses (e.g., apparatuses with chips that integrate multiple, traditional macroscopic laboratory processes) integrated into currency counters at all financial institutions throughout the world, the apparatuses linked into a data collection, analysis, and graphical information system to provide early warning to enable security activities. Although, in the preferred embodiment, currency is sampled and tested, any item that is ubiquitous in its occurrence, handling, and transportation throughout the world may be sampled and tested. Further, as items utilized for the exchange of goods or services, cards, such as credit or debit cards and identification documents, are generally included under the term "currency" herein.

Components that may be utilized in the practice of the present invention include proprietary and non-proprietary systems and devices known in the art, or that will become known as they are developed, for the detection of targeted substances. For example, U.S. Pat. No. 6,870,234 (to Brewer et al.) discloses a concentrator for remotely detecting biological and chemical materials, U.S. Pat. No. 6,730,212 (to Yamagishi et al.) discloses a sensor for the detection of biological pathogens and chemical agents in air, U.S. Pat. No. 6,447,991

(to Daitch et al.) discloses an aerogel for the detection of bio-aerosols, and U.S. Pat. No. 6,729,196 (to Moler et al.) discloses a sampling unit for the detection of particulates, including biological organisms, from gaseous fluids such as air. In the preferred embodiment of the present invention, such sensor devices are incorporated into the multifunctional detection apparatuses of the present invention for exposure to targeted substances.

Also provided in an embodiment of the present invention is a traffic tracking and scheduling system utilizing data from the biological detection system in combination with a system of notification, scheduling, and monitoring to enhance the ability of authorities to ensure security and efficient trade movement, particularly as trade items approach boundaries and borders. The boundary/border security component of the invention provides for generally uninterrupted movement of traffic with automated inspection of cargos conducted by redundant multifunctional detection devices that are loaded onto vehicles upon entry into a secure, geographically large, security corridor and removed upon completion of transit if no problems are detected during inspection. In the event of a confirmed security incident, the system provides for isolation, containment, and neutralization of the problematic cargo, and decontamination of the vehicle.

Thus, the present invention provides practical options for the world's health and hazardous substance security operatives by providing an infrastructure for efficient and effective early warning of emerging biological threats and for monitoring, interdicting, containing, and neutralizing those threats.

The present invention can be understood more effectively by considering the global credit card networks. For example, all members of the global BANC card network (BANC) could modify the cards they issue to include a bio-sensor that when handled would detect and transfer bio-data to their central computers as the cards are scanned in the process of making a purchase. Given the global use of computerized credit systems, data acquired during the use of those systems can be analyzed and presented graphically in mapping overlays for much of the world. In this example, the financial information BANC currently assembles can be used to provide a simple example of how biological activity might be analyzed and presented.

Not everyone in the world has a BANC card. However, with some very rare exceptions, everyone handles currency/ legal tender. Paper currency contains much biological activity. Much of that biological activity is idiosyncratic to regions and countries, and much of that activity would be considered background noise. With rare exceptions, the paper currency that people handle makes its way to banking and other financial institutions. Those institutions sort and count that currency daily (or more frequently). During counting, the currency can be passed over bio-sensors (designed into or initially attached as add-ons to existing devices) to detect biological activity.

Thus, an embodiment of the present invention provides for exposing currency (including, as used herein, other forms of tender such as credit cards) to multifunctional detection apparatuses comprising sensors. For example, such detection apparatuses may comprise lab-on-chip devices. Further, targeted substance attractors or concentrators may be incorporated into currency to enhance detection. Data gathered from the currency during the counting process is preferably forwarded directly to security personnel or to an analysis center (by internet or proprietary network) for analysis. Information is preferably displayed as overlays on maps at appropriate scales for use in bio-security related activities. Following counting (and extraction of biological material), currency is preferably sterilized ("bio-scrubbed") prior to returning it to circulation. The sterilization process enhances the sensitivity and reliability of data gathered and, over time, suppresses the inevitable background noise. Over the longer term, currency is preferably designed to incorporate more bio-sensitive tags to enhance the reliability of the process.

Another embodiment of the present invention provides for a traffic and border crossing system referred to herein as BIOTRAC. Each item (whether animal or inanimate) that is shipped/transported is labeled with a unique identifier. The item's identity is used by the shipper and the item is tracked as the item is transported.

Another embodiment of the present invention comprises a scheduling/monitoring system for all international shipments. Each transporter files, preferably electronically, a transit plan request with a border transit authority from the transporter's nominal point of origin. The transit plan preferably includes a cargo manifest, the final destination, the preferred border crossing, and the preferred time of arrival (PTA) at that crossing.

The travel plan request is processed and returned electronically by a border traffic control entity. Variations from a requested travel plan would reflect such considerations as previously scheduled traffic, bio-security issues with the cargo (possibly as a result of issues arising from bio-monitoring in the region), and knowledge of issues such as anticipated highway and weather conditions along the proposed route. At designated monitoring points en route, the system provides schedule adjustments, advisory notices, designated arrival time, and final border crossing gate information.

The small burden such a system places on suppliers, shippers, and buyers is offset by the value of minimal delay, smooth passage though the border, and timely delivery of cargo in the best possible condition. The tracking and scheduling in combination with the bio-monitoring embodiment of the present invention, constitute a substantial paradigm shift—from reactive and insular to proactive and global.

An embodiment of the present invention comprises a system referred to herein as BIOWALL to address problems inherent in transporting items across international borders. The BIOWALL is more appropriately characterized as a transit corridor than a border "crossing" given that it is not a discrete border crossing with inspection facilities and personnel. The BIOWALL comprises a physical, geographical corridor preferably comprising multiple, parallel, widely separated, directionally dedicated routes passing through an isolated area straddling an international border such as the Mexico/U.S. border. The site for the BIOWALL is preferably sufficiently large (for example, approximately 40 miles by 60 miles) to allow for traffic isolation while in transit and the location of isolated turn-out, bio-hazard inspection facilities en route to handle emergencies.

In an embodiment of the present invention, the basic protocols for the operation of the corridor are integrated with other embodiments of the present invention for the detection of target substances and anomalies in data indicating the presence of a threat.

Traffic through the BIOWALL is preferably scheduled to minimize congestion and to isolate shipments from biologically problematic origins—on both sides of a border. Preferably, routine aspects of the current shipment inspection system (for livestock or commodities) are largely automated and will incorporate the most advanced biological activity detection systems available. Upon arrival of a vehicle (for example, a cattle truck, container, etc.) at its designated point of entry, bio-sensing equipment is placed in the vehicle's cargo hold.

The vehicle then proceeds at a designated speed through the corridor while testing of the vehicle's cargo takes place. Testing is preferably monitored by telemetry as the vehicle proceeds. If no suspicious bio-activity is detected during transit through the bio-wall, the vehicle proceeds to the exit point where the monitoring equipment is removed. The vehicle is then cleared to continue on its way.

When telemetry readings produce suspicious results, the vehicle is diverted to a secure bio-hazard inspection area for additional testing. If initial tests are determined to be false positives, the vehicle is allowed to proceed. When additional testing and inspection confirm the presence of a disease or biological contamination, the vehicle and cargo are secured and are then moved along a dedicated route to central facilities where the cargo is destroyed and the vehicle is decontaminated.

In addition to providing the highest, technically possible level of detection, monitoring, and regulating, the present invention is extremely commerce-friendly. The BIOWALL handles large volumes of traffic in both directions. When biologically significant events occur, those events are readily isolated. At no time is other traffic disrupted, and clean shipments are able to continue toward their destinations—in all likelihood without any awareness by other transporters of those events, and without any concern of being compromised by delays or cross contamination.

Referring now to the figures, FIG. 1 shows three main components of an embodiment of the present invention, biological activity monitoring component (herein referred to as BIOSENTRI) 1, tracking and border transit scheduling component (herein referred to as BIOTRAC) 2, and boundary/border security component (herein referred to as BIOWALL) 3.

Preferably, BIOSENTRI 1 informs (by way of systemic interactions) the activities of BIOTRAC 2 and BIOWALL 3 and directly, and preferably, the activities of End Users 4. End Users 4 comprise at least one security entity such as, but not limited to the United States Department of Homeland Security (US DHS), the United Nations World Health Organization (UN WHO), the United Nations Food and Agriculture Organization (UN FAO), the United States Centers for Disease Control (US CDC), the United States Department of Agriculture (USDA), the World Organization for Animal Health (OIE), the United States Central Intelligence Agency (CIA), and INTERPOL.

Preferably, BIOWALL 3 informs (by way of systemic interactions) the activities of BIOSENTRI 1, BIOTRAC 2 and directly, and preferably, the activities of End Users 4.

Preferably, End Users 4 interact with BIOSENTRI 1, BIOTRAC 2 and BIOWALL 3 directly, and preferably, in such a manner as to inform and request information and services of both a peculiar and idiosyncratic nature which may at times, and as appropriate, require revision of protocols and reprogramming of hardware and software to address and respond to the information and requests.

Figure 2:
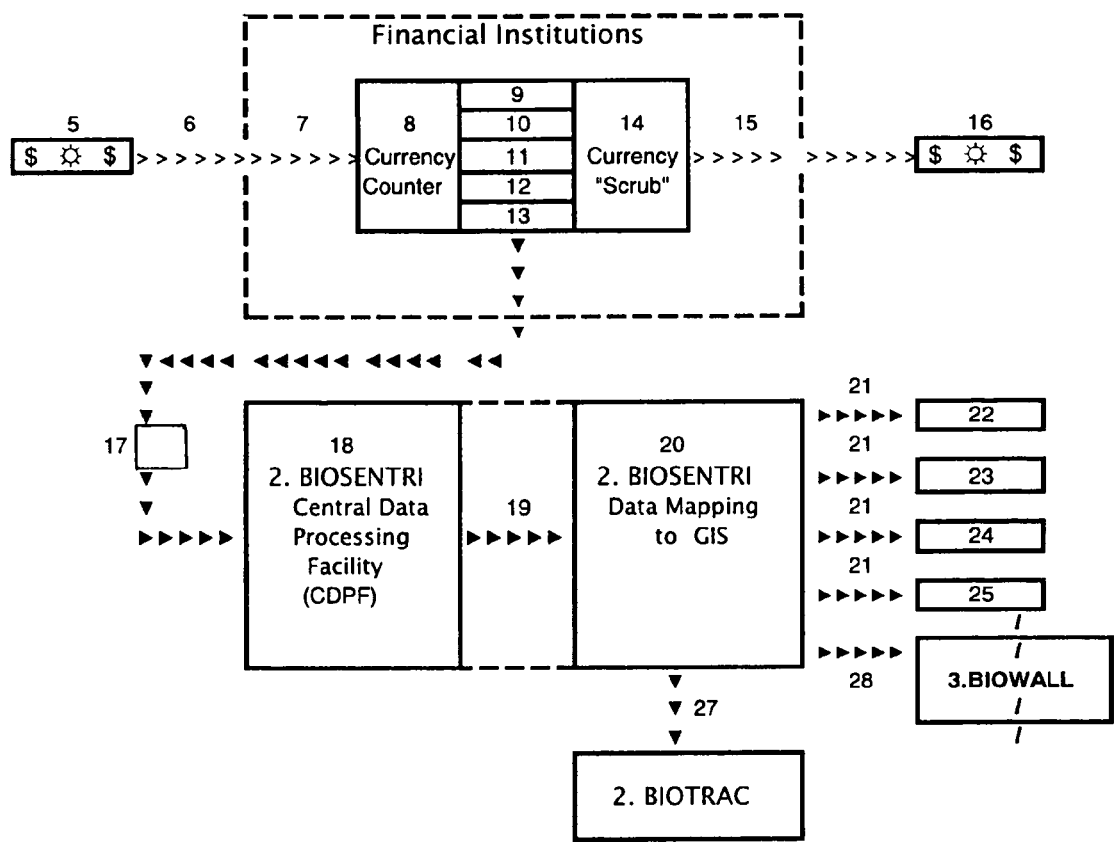
FIG. 2 is a schematic of an embodiment of the functional layout and operational protocols related to biological activity.

Referring now to FIG. 2, the biological activity detection component of an embodiment of the invention comprises common paper currency 5 in general circulation which serves as a collection medium for biologically active materials (and other chemicals and toxic substances or targeted substances). Currency 5 is regularly delivered via transportation mediums 6 (including, but not limited to, individuals and business organizations) to financial institutions 7 where it is accumulated and placed in or on devices 8 which count and/or sort currency 5. Notably, the process of counting and/or sorting currency 5 involves rapid "flipping" and/or "shuffling" of currency 5 which disturbs, and causes to become airborne, microscopic amounts of any and all substances on currency 5, whether biological, chemical, radiological or otherwise, that are attached to or caught in the matrix of materials that make up currency 5.

While airborne, such substances are available for sampling and testing. However, to insure their availability, integrated device 9 preferably enhances the movement of ambient air through currency 5 and directs the air to sensors 10 for sampling and testing. Sensors 10 are retrofitted to, or integrated into, currency counter 8. Preferably, sensors 10 are redundant and may be target specific or broad spectrum in nature. Sensors 10 may comprise non-proprietary, off-the-self technology and are preferably remotely re-configurable within specified parameters. Further, sensors 10 (and components 9, 11, 12, 13) of currency counter 8 are preferably designed as, or into, a modular "plug-and-play" configuration so that replacements for failure and upgrades can be made with minimal or no technical expertise, including by agents of international package carriers such as United Parcel Service, Federal Express, and DHL.

Preferably, currency counter 8 incorporates redundant devices 11 and technology for precise global positioning (GPS) functionality to add geographic parameter data to any and all data collected from currency 5 by sensors 10.

Preferably, currency counter 8 incorporates redundant "plug-and-play" module 12 for such use and technology as may become available during the practical functional life of currency counter 8.

Preferably, currency counter 8 incorporates redundant wireless or hard-wired internet or dedicated network access component 13 in communication with data transmission component 17 for the transmission of data collected by sensors 10, GPS 11 and other mapping apparatuses/systems 12 to central data processing facility (CDPF) 18 for analysis.

Preferably, currency counter 8 includes currency scrubber 14 to "bio-scrub", or otherwise sterilize (by chemical, electromagnetic, or other process), currency 5 prior to returning currency 5 to currency stream 15 in the form of sterilized currency 16. Preferably, as currency 5 wears out and is recalled and destroyed, it is replaced with newly designed currency comprising enhanced features for collecting targeted substances and subsequent sterilization.

Preferably, data collected by sensors 10 and sent to CDPF 18 is processed at CDPF 18 to identify and "ignore" local/regional specific background "noise" and to isolate targeted biological pathogens, other targeted data, or anomalous data to the extent that such information can be extracted from the raw data received.

Preferably, data of interest with its geographic coordinates is forwarded via communications stream 19 from CDPF 18 to geographical information system (GIS) unit 20 for mapping into a multi-layered GIS system. GIS unit 20 is displayed as overlays on real time graphical displays (on site, at other dedicated venues, and, if appropriate, on the Internet) at appropriate scales to inform bio-security and security-related entities and activities. Preferably, such graphical presentation of the information and other manifestations appropriate to need are sent via transmission stream 21 to contracted entities and organizations 22, 23, 24, and 25 and specifically sent via transmission stream 27 to BIOTRAC traffic tracking and scheduling component 2 and via transmission stream 28 to BIOWALL boundary/border security component 3. Entities and organizations 22, 23, 24, and 25 preferably include, but are not limited to, those designated as End Users 4 shown in FIG. 1.

Figure 3:
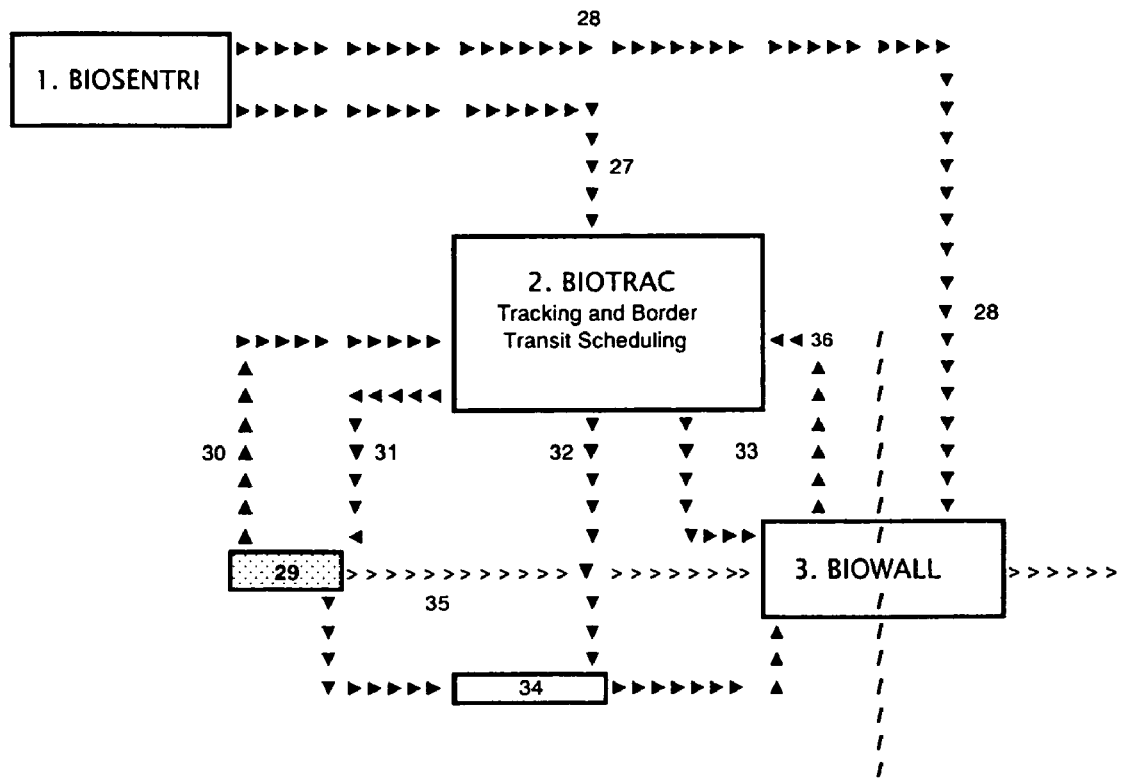
FIG. 3 is a schematic of an embodiment of the functional layout and operational protocols related to traffic tracking and scheduling.

Referring now to FIG. 3, the tracking and border transit scheduling component of an embodiment of the present invention comprises protocols for managing and tracking overland transport similar to those utilized for international civil air traffic. Prior to embarking on a trip that includes crossing a controlled border (international or otherwise), ground transport vehicle (GTV) 29 preferably files transit plan 30 with tracking and border transit scheduling component of BIOTRAC 2. Transit plan 30 includes such information as point of origin, cargo, preferred border transit point, preferred time of departure, estimated time of arrival at the border, and preferred route to the border.

Preferably, BIOTRAC 2, informed by BIOSENTRI 1, responds via transmission streams 31, 32, and 33 to GTV 29, to intermediate system checkpoints 34, and to BIOWALL 3. BIOTRAC 2 provides GTV 29 with specific route 35 from point of origin to border, intermediate checkpoints 34, designated border transit route, and time "window" for arrival at specified Point of Entry (POE) 37 (shown in FIG. 4). Preferably, and irrespective of requested transit plan 30, GTV's 29 proposing to transit from points of origin determined to be "problematic" based on information provided by BIOSENTRI 1 are required to transit the border at BIOWALL 3 installation to ensure the optimum level of security.

Figure 4:
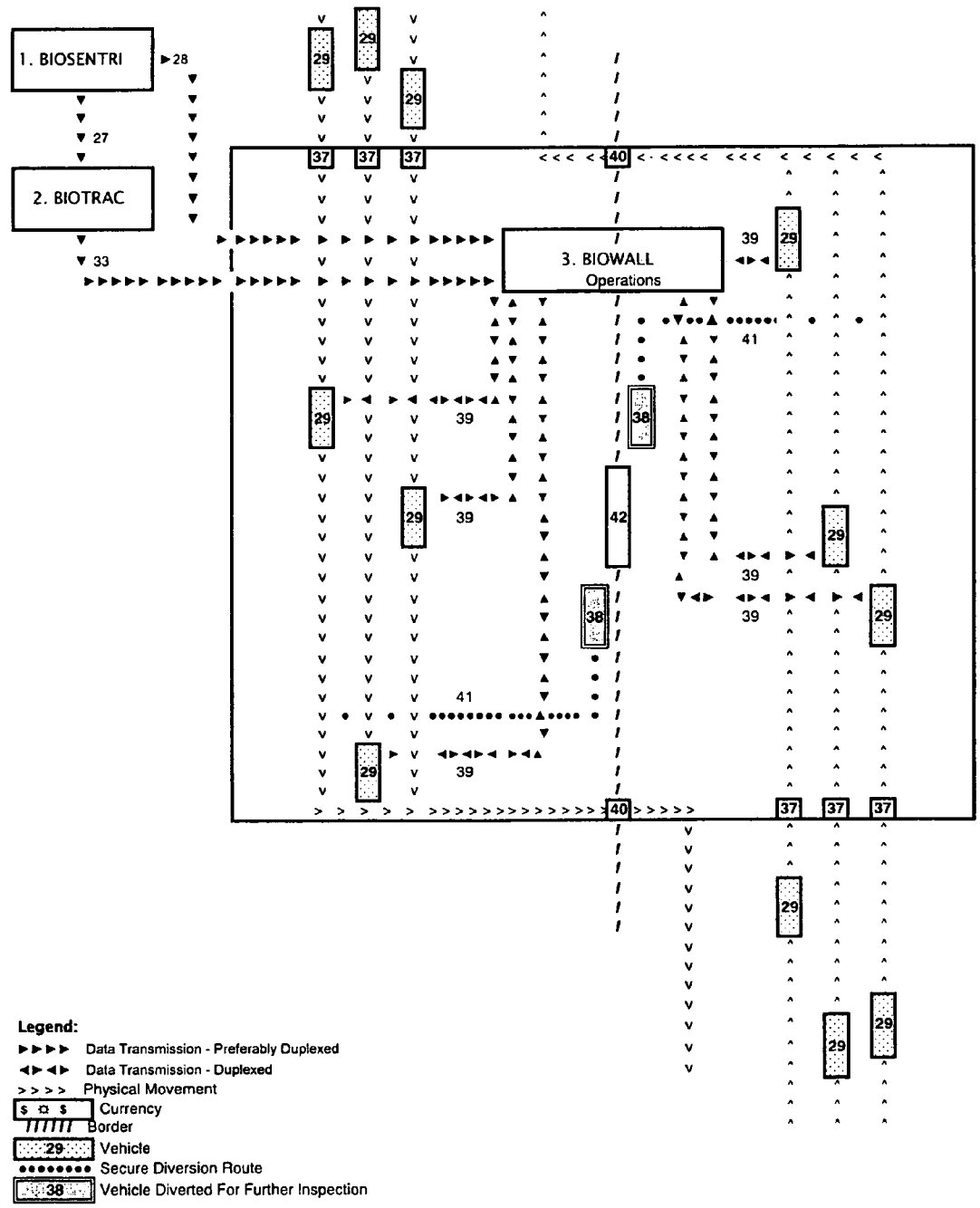
FIG. 4 is a schematic of an embodiment of the functional layout and operational protocols of boundary/border security.
Figure 5:
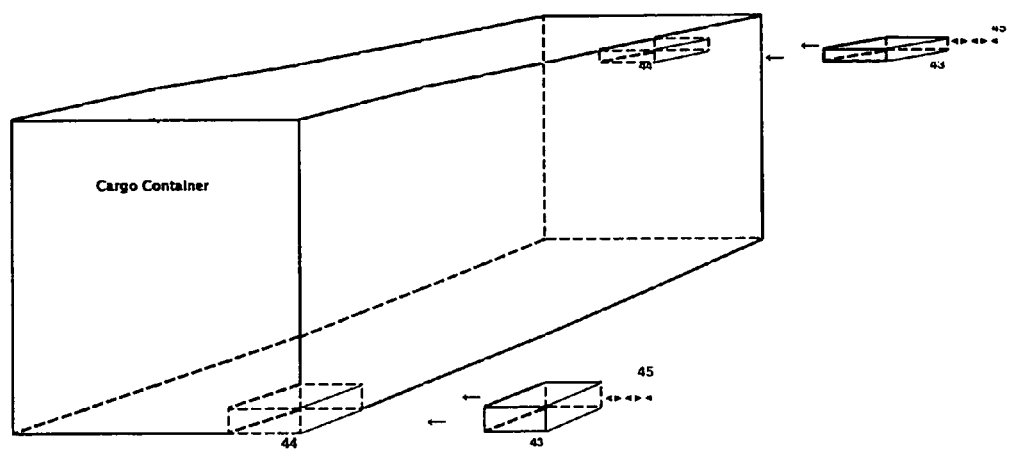
FIG. 5 shows a cargo container with modifications and/or original equipment to receive modular sensor/transmitter units for remote inspection of a container.

Referring now to FIGS. 4 and 5, the boundary/border security component of an embodiment of the invention comprises infrastructure and protocols for remotely inspecting GTV's 29 while such are in motion and a physically secure ground transit corridor of varying geographical dimensions but sufficiently large as to provide that the transit time of GTV 29 moving at approximately 20-30 miles per hour is approximately one hour. The embodiment preferably comprises infrastructure and protocols for the secure, non-disruptive diversion of GTV's 38 containing problematic cargos through route 41 and the isolation of GTV's 38, at facilities 42 for the containment, destruction and disposal of cargos found to be contaminated with pathogens or other dangerous or toxic materials. Facilities 42 are preferably utilized for the detoxification and clean-up of GTV's 38.

Preferably, GTV 29, having followed the specific instructions from BIOTRAC 2, arrives at designated BIOWALL POE 37 within the specified time "window".

Preferably, at POE 37, GTV 29 is visually inspected while technicians insert modular plug-in sensor units 43 into standardized receptacles 44 built into the structure of GTV 29 and its cargo holding areas.

Preferably, sensor units 43 incorporate varying arrays of redundant, multifunctional sensor devices (preferably and generally similar to sensors 10 used with BIOSENTRI 1) and are located in the cargo holds, or other cavities, of the GTV 29. Preferably these units also will employ non-proprietary, off-the-self technology. Such technology is preferably continually subjected to upgrade to insure that the most effective technology is being used. However, and preferably, units 43 differ in one respect from those used in BIOSENTRI 1 in that units 43 incorporate functions to actively extract ambient air/gases from the interior of the cargo holds and other cavities of GTV 29 and from the vicinity of live animals to capture respiratory gases. Further, units 43 preferably, and where appropriate, injects or emits "marker/catalyst" gases or substances into the cargo holds or cavities to enhance the capacity of sensor units 43 to capture targeted substances.

Preferably, modular units incorporate wireless data transmission stream 45 functionality, and, preferably, units 43 are part of a system and appropriate infrastructure for transmitting data via transmission stream 39 extracted by the multifunctional sensors loaded onto transiting GTV's 29 to BIOWALL 3 operations which receives, processes, and responds, in real time, via transmission stream 39 to the results of the data analyses.

Preferably, once loaded with modular sensor/transmitter units 43, GTV 29 departs the POE 37 and proceeds on its designated route through the BIOWALL 3 corridor, in isolation from other GTV's 29 while the sensor/transmitter units inspect the GTV 29 and its cargo.

Preferably, the remote inspection proceeds uneventfully as GTV 29 transits the BIOWALL 3 corridor in isolation. Preferably, GTV 29 arrives at Exit 40 Checkpoint/Border Crossing (EBC), the sensor/transmitter units 43 are removed, and GTV 29 is cleared to cross into the next jurisdiction/country.

Preferably, the sensor/transmitter units 43 are then recalibrated, cleaned, and serviced as appropriate, and delivered to the adjacent POE's 37 for re-employment.

Alternatively, and preferably, in the event that the remote inspection identifies the presence of targeted substances, chemicals or identifies anomalies, GTV 38 is diverted from the main transit route onto secure diversion route 41 for more intensive inspection.

Preferably, when the more intensive inspection of GTV 38 is positive for targeted material, GTV 38 and cargo are routed to secure disposal facilities 42.

Preferably, upon arrival at secure disposal facilities 42, the cargo is inspected, documented, and disposed of as appropriate to the nature of the pathogen, chemical, or other substance identified. Sensor/transmitter units 43 are removed, cleaned, serviced, and if appropriate, recalibrated and returned to service. GTV 38 is "scrubbed" and if possible made ready for return to service. GTV 38 operator is dealt by the relevant authorities as appropriate to the nature of the incident.

The preceding examples can be repeated with similar success by substituting the generically or specifically described compositions, biomaterials, devices and/or operating conditions of this invention for those used in the preceding examples.

Although the invention has been described in detail with particular reference to these preferred embodiments, other embodiments can achieve the same results. Variations and modifications of the present invention will be obvious to those skilled in the art and it is intended to cover all such modifications and equivalents. The entire disclosures of all references, applications, patents, and publications cited above, and of the corresponding application(s), are hereby incorporated by reference.

What is claimed is:

1. A system for monitoring the activity of a targeted substance on a stream of currency comprising:

at least one multifunctional detection apparatus integrally disposed in a currency counter and currency shuffler device for disturbing the targeted substance and causing the targeted substance to be airborne;

said at least one multifunctional detection apparatus comprising at least one substance sensor for sampling and testing the targeted substance airborne from the stream of currency;

an apparatus for processing the stream of currency comprising an integrated apparatus enhancing movement of ambient air past the currency and directing the air to said at least one sensor for sampling and testing, wherein said sensors are remotely re-configurable; and at least one data transmission component for transmission of data collected by the at least one sensor to a central data processor which processes said data from said transmission, said data processor comprising at least one computing component for processing transmitted data in real time to identify and ignore background noise and isolate and identify the targeted substance.

2. The system of claim 1 further comprising at least one targeted substance attraction component disposed in the currency to enhance detection by said at least one multifunctional detection apparatus.

3. The system of claim 1 further comprising a currency counter through which the stream of currency passes and in which said at least one multifunctional detection apparatus comprises at least one chip that integrates a traditional macroscopic laboratory process.

4. The system of claim 1 wherein said data transmission component communicates with a global positioning system.

5. The system of claim 1 wherein the targeted substance comprises a biological, chemical, or radiological substance.

6. The system of claim 1 further comprising a secure communications transmission infrastructure linking said at least one multifunctional detection apparatus with the central data processor.

7. The system of claim 1 further comprising an infrastructure comprising a system for forwarding data of interest with its geographic coordinates from said data transmission and mapping said information to a multilayered geographical information system in communication with security personnel.

8. The system of claim 7 further comprising a central facility linking said multilayered geographical information system to security personnel to, in real time, graphically communicate said mapping information to the security personnel and to integrate said information with geographic specific data.

9. The system of claim 8 wherein said geographic specific data comprises data selected from the group consisting of weather data, topography data, security response capability data, demographic data, geo-political data, agricultural data, and a combination thereof.

10. The system of claim 1 further comprising a purging apparatus for removing the targeted substance from the currency.

11. A method for monitoring the activity of a targeted substance on currency comprising:
providing at least one multifunctional detection apparatus comprising at least one modular remotely re-configurable sensor for detecting a targeted substance airborne from the currency;
integrally disposing the at least one multifunctional detection apparatus into a currency counter and currency shuffler device;
shuffling the currency and disturbing the targeted substance and causing the targeted substance to be airborne;
moving ambient air past the currency and directing the air and airborne targeted substance to the sensor;
sampling and testing the targeted substance airborne from the currency;
adding geographic specific data to data collected from the currency by the sensor;
communicating about the targeted substance between the at least one multifunctional detection apparatus to a global positioning system, an Internet system, or a bi-directional data transmission system; and
transmitting the data to a central data processor.

12. The method of claim 11 further comprising disposing a targeted substance attraction component in the currency to enhance detection by the multifunctional detection apparatus.

13. The method of claim 11 further comprising:
providing a currency counter;
disposing the at least one multifunctional detection apparatus in the currency counter;
passing the stream of currency through the currency counter; and
detecting the targeted substance on the currency.

14. The method of claim 11 wherein the targeted substance comprises a radiological, biological, or chemical substance.

15. The method of claim 11 further comprising linking the detection apparatus with the central data processor via a secure communications transmission infrastructure.

16. The method of claim 15 further comprising disposing computing components in the central data processor and processing the data transmitted in real time to screen out background noise and to isolate and identify the targeted substance.

17. The method of claim 15 further comprising:
linking a mapping infrastructure with the central data processor;
sending geographic specific data from the central data processor to the mapping infrastructure; and
mapping the information to a multilayered geographical information system in communication with security personnel.

18. The method of claim 17 further comprising:
providing a central facility linking the multilayered geographical information system to security personnel;
graphically communicating the mapping information to the security personnel in real time; and
integrating the information with geographic specific data in real time.

19. The method of claim 17 wherein the geographic specific data comprises data selected from the group consisting of weather data, topography data, security response capability data, demographic data, geo-political data, agricultural data, and a combination thereof.

20. The method of claim 11 further comprising purging the currency stream to remove the targeted substance from the currency stream.

21. The system of claim 1 wherein the targeted substance comprises a pathogen.

22. The method of claim 11 wherein the targeted substance comprises a pathogen.

23. The system of claim 1 wherein said data transmission component communicates with an Internet system.

24. The system of claim 1 wherein said data transmission component communicates with a bi-directional data transmission system.

* * * * *